(12) United States Patent
Lefevre et al.

(10) Patent No.: US 8,652,513 B2
(45) Date of Patent: Feb. 18, 2014

(54) FILM-FORMING STARCHY COMPOSITION

(75) Inventors: Philippe Lefevre, Haverskerque (FR); Alain Francois, Drouvin le Marais (FR); Philippe Facon, Estaires (FR); Claude Quettier, Lambersart (FR); Xavier Parissaux, Arques (FR)

(73) Assignee: Roquette Freres, Lestrem (FR)

( * ) Notice: Subject to any disclaimer, the term of this patent is extended or adjusted under 35 U.S.C. 154(b) by 736 days.

(21) Appl. No.: 10/579,919

(22) PCT Filed: Aug. 18, 2004

(86) PCT No.: PCT/FR2004/002158
§ 371 (c)(1),
(2), (4) Date: May 19, 2006

(87) PCT Pub. No.: WO2005/060944
PCT Pub. Date: Jul. 7, 2005

(65) Prior Publication Data
US 2007/0110799 A1    May 17, 2007

(30) Foreign Application Priority Data
Nov. 20, 2003 (FR) .................................... 03 13604

(51) Int. Cl.
*A61K 9/36* (2006.01)
*A61K 9/48* (2006.01)
*A61K 31/70* (2006.01)
*A61K 31/718* (2006.01)

(52) U.S. Cl.
USPC .......................... 424/451; 424/480; 106/206.1

(58) Field of Classification Search
USPC .......................................... 424/443, 451, 480
See application file for complete search history.

(56) References Cited

U.S. PATENT DOCUMENTS

| | | | |
|---|---|---|---|
| 3,281,411 A | | 10/1966 | Therese et al. |
| 4,431,800 A | * | 2/1984 | Leusner et al. ............... 536/111 |
| 5,498,706 A | | 3/1996 | Frische et al. |
| 6,123,963 A | * | 9/2000 | Kim et al. ..................... 424/482 |
| 6,469,161 B1 | * | 10/2002 | Fuertes et al. ............... 536/55.3 |
| 7,118,764 B2 | | 10/2006 | Carbone et al. |
| 2002/0032254 A1 | * | 3/2002 | Haasmaa et al. ................. 524/47 |
| 2003/0029444 A1 | | 2/2003 | Carbone et al. |
| 2003/0099692 A1 | * | 5/2003 | Lydzinski et al. ............ 424/443 |

FOREIGN PATENT DOCUMENTS

| | | |
|---|---|---|
| CA | 2086410 A1 | 10/1992 |
| EP | 0638609 A2 | 2/1995 |
| EP | 0669369 A1 | 8/1995 |
| EP | 0 735 080 | 10/1996 |
| EP | 0 945 487 | 9/1999 |
| EP | 1 245 577 | 10/2002 |
| JP | 05508185 A | 11/1993 |
| JP | 08325943 A | 12/1996 |
| JP | 09194501 A | 7/1997 |
| JP | 2002532600 A | 10/2002 |
| JP | 2003221752 A | 8/2003 |
| JP | 2004519546 A | 7/2004 |
| WO | 90/13576 | 11/1990 |
| WO | 99/21536 | 5/1999 |
| WO | 00/36006 | 6/2000 |
| WO | 0036006 A1 | 6/2000 |
| WO | 01/92400 | 12/2001 |
| WO | 02/00205 | 1/2002 |
| WO | 02077035 A1 | 10/2002 |

OTHER PUBLICATIONS

McCready et al., Determination of Starch and Amylose in Vegetables, Analytical Chemistry, 1950, 22(9), pp. 1156-1158.*
Funke et al., "Eigenschaften von Gießfilmen aus nativen and Chemisch modifizierten Starken", 1994, vol. 46, No. 10, pp. 384-388.
Abstracts of Papers 225th ACS National Meeting New Orleans, Cell-013, p. 2/E.
Cereal Food World, 1996, vol. 41, No. 7, p. 579.
Glittenberg et al., "Customised coating starches for optimization of coater runnability and paper quality", Cerestar, Euro Centre Paper, 1995, vol. 36, No. 9, pp. 18-20 and 22-24.
Jeon et al. "The suitability of barley and corn starches in their native and chemically modified forms for volatile meat flavor encapsulation", Food Research International, 2003, vol. 36, pp. 349-355.
Lawson et al., "Gum Arabic Replacement in Confectionery Applications", Spec. Publ. R. Soc. Chem., 1988, No. 218.
Szczodrak et al., "Starch-Lipid Interactions and Formation of Resistant Starch in High-Amylose Barley", Cereal Chem. vol. 69, No. 6, pp. 626-632.
Zhao et al., "Novel High-Performance Materials from Starch. 3. Influence of Degree of Substitution and Amylose/Amylopectin Ratio on Performance", Chem. Master., 1998, vol. 10, No. 3, pp. 804-811.
Wolff et al. "Triesters of Corn Starch, Amylose, and Amylopectin", Journal of Industrial and Engineering Chemistry, 1951, vol. 43, No. 4, pp. 911-914.
Japanese Office Action, dated Apr. 12, 2011, from corresponding JP application.

* cited by examiner

*Primary Examiner* — Lezah Roberts
*Assistant Examiner* — Tracy Liu
(74) *Attorney, Agent, or Firm* — Young & Thompson

(57) ABSTRACT

A film-forming starchy composition for the film-coating of solid forms or the preparation of films. The inventive composition has an amylose content of between 25 and 45%, preferably between 30 and 44% and still more preferably between 35 and 40%, the percentages being expressed by dry weight in relation to the dry weight of starch contained in the composition, and includes at least one stabilized starch. A method for the film-coating of solid forms is disclosed and includes spraying the film-forming composition onto a moving nuclei bed. The film-forming composition is used for the production of films and capsules.

17 Claims, No Drawings

FILM-FORMING STARCHY COMPOSITION

A subject matter of the invention is a starch-based film-forming composition and a process for the film-coating of solid pharmaceutical, food or agricultural forms, and for the preparation of films employing said composition.

The term "solid forms" is understood to mean, within the present invention, any presentation of food, pharmaceutical, cosmetic, chemical or agrochemical substances in the form, for example, of tablets, capsules, including hard gelatin capsules, pellets, microspheres, granules, seeds, crystals or powders, and the like.

Native and modified starches are conventionally used in the pharmaceutical industry, in particular as diluent, disintegrating agent or binder, for the preparation of tablets or for filling hard gelatin capsules. Native starches are rarely used for film-coating due mainly to their insoluble nature in cold water, which necessarily requires a preliminary precooking of the starch in order to dissolve it.

The film-coating of solid forms, in particular of tablets, is a frequent operation aiming at obtaining physical and chemical protection of the active principle. The medicament is thus protected from its environment (moisture, oxygen, light). Film-coating also makes it possible to mask the taste, the odor or the color of this active principle, and also makes it possible to modify its release in the body by increasing the resistance of the tablet to gastric juices. Film-coating facilitates the ingestion of the tablets and improves their appearance and their mechanical soundness. The majority of the solid forms can be film-coated: tablets, capsules, including hard gelatin capsules, or granules.

Film-coating consists of the application of a film-forming liquid composition, for example to tablets, this composition becoming, after drying, a protective film. The ideal film-forming agent preferably exhibits a high molecular weight, a low viscosity and good adhesion to the substrate. It should make it possible to obtain an elastic and cohesive film which adheres to the form which it coats. It is preferably soluble in water, water being the preferred solvent, in comparison with organic solvents, due to its ease of use.

A good number of film-forming compositions based on cellulose or acrylate polymers exist on the market. Mention may in particular be made of hydroxypropyl methylcellulose (HPMC), commonly used for the film-coating of tablets. Some difficulties may be encountered on using polymers of this type, such as problems of adhesion to the substrates, of cracking or splitting of the coating, or phenomena of filling the incised lines often present on tablets (logos, dosages). Furthermore, HPMC exhibits the disadvantage of having an unpleasant taste and/or odor. In addition, the synthetic polymers are made available commercially at fairly high prices.

Starch has been used for a long time as film-forming agent in the textile or paper industry. The main industrial sources of starch are, in order of decreasing importance, corn, wheat, potato, manioc and sweet potato. Starch exhibits variations in composition, in particular as regards the percentages of amylose and of amylopectin, depending on its origin. Amylopectin is the branched component of starch where the $\alpha$-D-glucose units are polymerized via $\alpha$-D-(1-4) bonds and are connected with $\alpha$-D-(1-6) branchings.

Amylose is the linear component of starch, which includes virtually only $\alpha$-D-(1-4) bonds.

Some varieties of starch, referred to as "waxy", are composed essentially of amylopectin. Others, referred to as "amylose-rich", are composed of more than 50% and generally of 70 to 75% of amylose.

Amylose-rich starches have been known for a long time for their film-forming properties and have always appeared superior to the other starches in this application. However, they exhibit the disadvantage of requiring processing at high temperature, i.e. approximately 80° C., in order to prevent these starches from retrograding. This is a particular nuisance in the coating of solid forms since conventional film-coating equipment is not designed to operate at such temperatures. Furthermore, care has to be taken that no point in the circuit is cold, which would cause the composition to gel in the circuits.

Amylopectin-rich starches cannot be used in particular in pan film-coating processes, given that, when they are used, the centers to be film-coated are observed to agglomerate together. This totally unacceptable failing is very difficult to correct, produces a heterogeneous and incomplete final coating and requires complex formulations. In addition, waxy starches are very viscous in solution, which probably explains the processing difficulties which they bring about in film-coating.

Patent WO 02/00205 discloses the use of acetylated and pregelatinized amylose-rich starch in the coating of tablets or the manufacture of capsules and caplets (tablets coated with a thick colored film resembling a hard gelatin capsule). The starch comprises more than 50% of amylose and preferably results from corn.

EP Patent 1 245 577, of which the Applicant Company is proprietor, discloses a process for the preparation of pregelatinized amylose-rich starches and their applications in film-coating, soft capsules, hard gelatin capsules or freshening films.

Patent WO 02/092708 discloses a process for the preparation of a film-forming composition comprising the extraction into an alcoholic medium of the amylose of a starch comprising more than 50% thereof. The film-forming composition thus comprises pure amylose and can additionally comprise a plasticizer.

EP Patent 945 487 discloses films based on starch derivatives or amylose derivatives manufactured from a solution of starch hydroxypropyl ether, the amylose content of the starting raw material being greater than 60%. In particular, a wrinkled pea starch comprising approximately 75% of amylose is used.

EP Patent 1 024 795 discloses mixtures of amylose and of ethylcellulose, the amylose alone not being stable with respect to water uptake.

Although the film-forming properties of amylose-rich starches are advantageous, their use remains fairly restricting in practice, due to their rapid retrogradation with cooling. This can be avoided by carrying out a hot spraying of the film-forming solution, but a risk then exists of blocking the nozzles due to the retrogradation of the starch during the spraying. Film-coating solutions based on synthetic polymers are currently prepared and sprayed at ambient temperature. It would thus be highly advantageous and much more practical industrially to provide a film-forming starch which can be employed at an operating temperature as close as possible to ambient temperature while remaining stable under these conditions. Another aim is to be able to manufacture a film or a film-coating of solid form which is impermeable to water, making it possible to formulate coatings which are a barrier to water or which possess delayed dissolution. Likewise, the formulator is looking to reduce the film-coating time, for the highest possible solids content and for a viscosity compatible with nozzle spraying, which can present problems when operating with amylose-rich starches which develop a high viscosity in solution. The ideal would be to provide a coating solution with a solids content of greater than 20% and preferably in the vicinity of 30% which exhibits a viscosity of less than 500 mpa·s at the operating temperature. This would make it possible to dispense with any heating stage and any with stage in which the solutions are kept hot.

There thus currently does not exist a satisfactory solution for producing satisfactory films or film-coatings from starches as sole film-forming agent in order to be able to replace the rather expensive synthetic polymers.

Seeking to overcome this deficiency, the Applicant Company then carried out numerous studies targeted at replacing all or part of the synthetic polymers with a starchy material not exhibiting the disadvantages of the abovementioned starches.

The Applicant Company has had the credit of finding that this aim could be achieved provided that use is made, in preparing a film-forming composition, of a starch or a mixture of starches having an amylose content selected within a specific range of between 25 and 45%.

A subject matter of the present invention is thus a film-forming starchy composition for the film-coating of solid forms or the preparation of films, characterized in that it exhibits an amylose content of between 25 and 45%, preferably of between 30 and 44%, more preferably still of between 35 and 40%, and better still between 35 and 38%, these percentages being expressed by dry weight with respect to the dry weight of starch present in said composition, and in that it comprises at least one stabilized starch.

Use may be made, in preparing said film-forming composition, of mixtures of starches of various origins, so as to regulate the amylose content between 25 and 45%. It is possible to mix, for example, amylopectin-rich starches (waxy starches) with amylose-rich starches.

Furthermore, it is possible to use starches naturally exhibiting an amylose content within the range selected according to the invention. In particular, the starch resulting from legumes may be suitable. In accordance with the present invention, this legume starch exhibits an amylose content of less than 45%, more specifically of between 25 and 45%, preferably of between 30 and 44%, and more preferably still of between 35 and 40%. The term "legume" is intended to mean, in the present invention, any plant belonging to the Caesalpinaceae, Mimosaceae or Papilionaceae families and in particular any plant belonging to the Papilionaceae family, such as, for example, pea, bean, broad bean, horse bean, lentil, alfalfa, clover or lupin.

This definition includes in particular all the plants described in any one of the tables present in the paper by R. Hoover et al. entitled "Composition, Structure, Functionality and Chemical Modification of Legume Starches: A Review".

Preferably, the legume is selected from the group consisting of pea, bean, broad bean and horse bean.

Advantageously, it is pea, the term "pea" in this instance being considered in its broadest sense and including in particular:
  all the wild varieties of smooth pea and
  all the mutant varieties of smooth pea and of wrinkled pea, this being the case whatever the uses for which said varieties are generally intended (food for man, animal nutrition and/or other uses).

Said mutant varieties are in particular those referred to as "mutants r", "mutants rb", "mutants rug 3", mutants rug 4", "mutants rug 5" and "mutants lam" as described in the paper by C-L Heydley et al. entitled "Developing Novel Pea Starches", Proceedings of the Symposium of the Industrial Biochemistry and Biotechnology Group of the Biochemical Society, 1996, pp. 77-87.

According to another advantageous alternative form, the legume is a plant, for example a variety of pea or of horse bean, giving seeds comprising at least 25%, preferably at least 40%, by weight of starch (dry/dry).

The term "legume starch" is understood to mean any composition extracted, this being the case in whatever way, from a legume and in particular from a Papilionaceae and having a starch content of greater than 40%, preferably of greater than 50% and more preferably still of greater than 75%, these percentages being expressed by dry weight with respect to the dry weight of said composition.

Advantageously, this starch content is greater than 90% (dry/dry). It can in particular be greater than 95%, including greater than 98%.

According to another variant, the protein content in said composition is less than 25%, preferably less than 10%, these percentages being expressed by dry weight with respect to the dry weight of said composition. This content can in particular be less than 5%, including less than 1%.

The starch content of the film-forming composition in accordance with the invention is between 10 and 90% by weight, preferably between 10 and 50%, and more preferably still between 10 and 30%.

The starch present in said composition can in particular have been subjected to at least one modification treatment selected from the group consisting of chemical treatments, physical treatments and enzymatic treatments.

The chemical treatments comprise in particular all the known operations of esterification, of etherification, of crosslinking or of hydrolysis by acid or oxidizing routes.

According to a preferred embodiment of the invention, the chemical treatments, which are particularly well suited to the preparation of a film-forming composition, are the "stabilizing" treatments, which are hydroxypropylation or acetylation; it being possible for these treatments optionally to be supplemented by a fluidification, for example by acid treatment. In this case, a film-forming composition is obtained which exhibits properties entirely similar to those of the reference synthetic polymer: hydroxypropyl methylcellulose. The composition according to the invention thus advantageously comprises at least one stabilized starch and preferably a hydroxypropylated starch exhibiting a degree of substitution (DS) of at most 0.2. The term "DS" is understood to mean, in the present invention, the mean number of hydroxypropyl groups per 10 anhydroglucose units. This mean number is determined by the standard analytical methods well known to a person skilled in the art.

The physical treatments comprise in particular all the known operations of precooking, of cooking, of extrusion, of atomization, of drying, of plasticizing or of granulation, or operations in which treatment is carried out with microwaves or ultrasound.

The film-forming composition in accordance with the invention can additionally comprise one or more secondary film-forming agents which can be selected from cellulose derivatives, such as alkyl ethers or alkyl esters, such as, for example, methylcellulose, carboxymethylcellulose (CMC), hydroxypropyl cellulose (HPC), hydroxypropyl methylcellulose, cellulose acetate phthalate, ethylcellulose or cellulose acetate, or also polyvinylpyrrolidone (PVP), poly(vinyl phthalate), dextrose, zein, pullulan, acrylic polymers, alginates, carrageenates, polyvinyl alcohol (PVA), gelatin, dextrins and mixtures thereof. This secondary film-forming agent has a reinforcing covering role and makes it possible to prevent possible cracking of the coating formed, including its detrimental change during subsequent handling operations.

Advantageously, use will be made of a hydroxypropyl methylcellulose of low viscosity (of between 3 and 15 centipoises at ambient temperature in solution at 2% by weight in water). According to a preferred embodiment, use will be made of a mixture of hydroxyethyl cellulose, of hydroxypropyl methylcellulose and of starch in accordance with the invention, the weight ratio of the hydroxyethyl cellulose to the hydroxypropyl methylcellulose advantageously being between 1:4 and 1:1, preferably between 1:3 and 1:2.

The secondary film-forming agent will be present in the film-forming composition in accordance with the invention at a level of 0 to 55% by weight on a dry basis, preferably of 3.5 to 50%, and more preferably still of 5 to 20%.

The film-forming composition in accordance with the invention can advantageously comprise one or more hydrophilic or hydrophobic plasticizers. This plasticizer can be selected from the group consisting in particular of glycerol, sorbitol and sorbitol anhydrides, maltitol and maltitol syrups, polyethylene glycol with a molecular weight of between 400 and 10 000 daltons and polyethylene glycol stearate, propylene glycol, triethyl citrate, acetyl triethyl citrate, tributyl citrate, polysorbate, acetylated monoglycerides, lactic acid esters, fatty acids and their salts or derivatives which are ethoxylated, such as, in particular, stearic acid, phthalates, ethyl sebacate, butyl sebacate, miglyol, glycerol triacetate, liquid paraffin, lecithin, carnauba wax or hydrogenated castor oil, alone or as a mixture with one another. A preferred plasticizer is ethoxylated stearic acid or triacetin.

Plasticizer contents of between 2.5 and 30% are highly suitable, the percentages being expressed with respect to the starch present in the film-forming composition. According to a preferred embodiment, the film-forming composition according to the invention comprises between 5 and 15%, and more preferably still between 7.5 and 10%, of plasticizer by dry weight with respect to the film-forming composition.

The film-forming composition can also comprise any appropriate additive commonly used by a person skilled in the art, such as flavorings, sweeteners, dyes or pigments, opacifiers, such as talc, lubricants, such as magnesium stearate, mineral oils, lecithin or carnauba wax, water-repelling agents, such as fatty acids and their derivatives, or silicone polymers, wetting agents, such as surface-active agents, surfactants, such as polysorbate 80, agents for improving the adhesion of the film, such as microcrystalline cellulose, polyols, maltodextrins, polydextrose or lactose, preservatives, such as, in particular, sodium citrate, release agents, such as polyethylene glycol 3350, lecithin, stearic acid, talc or microcrystalline cellulose, aqueous solvents, such as methanol, ethanol, butanol, methylene chloride or acetone, and active substances, for example pharmaceutical active substances.

The coloring pigments capable of being used can be selected from the pigments used to date in the manufacture of film-forming products intended for the coating of solid pharmaceutical or food forms. Use may be made of any pigment or dye which are soluble or in the form of lakes, of food or pharmaceutical grade, and in particular titanium dioxide, talc, magnesium carbonate, iron oxides or riboflavin. The dye contents vary according to the type of coloring desired: for white coatings, it will be preferable to use 20 to 50% by weight of titanium dioxide; for colored coatings, use will be made of 0.1 to 40%, preferably 15 to 25%, by weight of dye.

The lubricating agents can be used in a proportion of 0 to 10% by weight in the film-forming composition. The preservatives are generally used in a proportion of 0 to 4% by weight. The surfactants are incorporated in a proportion of 0 to 15% by weight.

The film-forming composition can additionally comprise water, and generally water contents of between 10 and 90% by weight. Preferably, said composition comprises from 60 to 85% by weight of water, and more preferably still from 70 to 80% of water.

The film-forming composition in accordance with the invention can also be provided in the form of a ready-for-use powder. It can consist either of a physical mixture of powders, or can be in the form of granules obtained by techniques known to a person skilled in the art, such as wet granulation, fluidized bed granulation, granulation by atomization, by extrusion, spheronization, compacting, spray-cooling, and the like.

Good results have been obtained with film-forming compositions comprising, by weight:
  10 to 15% by weight of stabilized pea starch
  1 to 2% by weight of plasticizer
  optionally approximately 5 to 7% of opacifier.

Very good results have been obtained with film-forming compositions comprising:
  10 to 15% by weight of hydroxypropylated pea starch
  1 to 2% of glycerol
  5 to 7% of talc
  the remainder to 100% being water and other additives, such as dyes and/or flavorings.

In the case where the composition according to the invention is provided in the form of a ready-for-use powder, the pulverulent composition advantageously comprises:
  from 15 to 75%, preferably from 25 to 50%, by weight of stabilized pea starch, preferably hydroxypropylated pea starch, and more preferably still hydroxypropylated and fluidification-treated pea starch,
  from 1 to 20% and preferably from 5 to 12% by weight of a secondary film-forming agent,
  from 5 to 15% by weight of a plasticizer,
  optionally 1 to 20% of an adhesion promoter, such as, in particular, lactose or microcrystalline cellulose.

According to a preferred embodiment of the present invention, the secondary film-forming agent is a cellulose derivative and the plasticizer is polyethylene glycol or polyethylene glycol stearate.

Other compositions suitable for various applications are described by way of illustration in the examples which follow.

The film-forming composition in accordance with the invention is advantageously used for the film-coating of solid forms, such as: tablets, capsules, including hard gelatin capsules, pellets, granules or seeds, of solid food forms, such as biscuits, breakfast cereals or confectionery, for preparing soft capsules or hard gelatin capsules, and for the manufacture of films intended for any food, pharmaceutical, agricultural, industrial and other applications. It may also advantageously be suitable for the coating of vitamins or active principles, in particular in the form of powders or crystals. It can act in protecting the active principle with regard to the environment (moisture, oxidation) or in masking taste, in particular in the presence of bitter active principles or active principles exhibiting an unpleasant taste, and can also delay the release of the active principle, in particular in combination with a hydrophobic plasticizer. In the case of seeds, the film-forming composition confers thereon a coating which protects with regard to the environment and in particular with regard to fungal or bacterial attacks.

It is particularly well suited to the preparation of films comprising active principles or aromatic films, also known as flavor strips. They are very thin films which, placed on the tongue, melt instantaneously while diffusing a flavor, for example of mint. They may also be suitable for pharmaceutical applications not specifically requiring instantaneous melting of the film, such as the optionally delayed release of active principles, for example, or mucoadhesion.

Thus, a film-forming composition in accordance with the invention, exhibiting a viscosity of less than or equal to 500 mpa·s at 25° C. and a solids content of 10%, makes it possible to solve the technical problem of the stability and ready processability of the starchy compositions of the prior art.

Amylose-rich or amylopectin-rich starch compositions all exhibit a viscosity such that, in solution at a solids content of 10% and 25° C., it is virtually impossible to use them in standard film-coating equipment. This is why the present invention is directed to a film-forming starchy composition suitable for the film-coating of solid forms or for the preparation of films, characterized in that it exhibits a viscosity of less than 500 mpa·s at 25° C. and a solids content of 10%.

The viscosity within the meaning of the present invention is a Brookfield viscosity determined by means, for example, of a Brookfield RVF 100 viscometer using the spindle of the device which gives a reading of between 20 and 80% of the scale of the dial of the device at a rotational speed of 100 revolutions per minute.

According to an advantageous variant, said starchy composition exhibits an amylose content of between 25 and 45%, preferably between 30 and 44%, more preferably still between 35 and 40%, and better still between 35 and 38%, by dry weight with respect to the dry weight of total starch.

The present invention is additionally directed to a process for the film-coating of solid forms, characterized in that it comprises the spraying of a film-forming composition according to the invention over a bed of moving cores. This is because the composition according to the invention makes it possible, entirely advantageously and in a novel fashion, to spray at ambient temperature, that is to say of the order of 20° C., which the compositions of the prior art did not make possible.

Furthermore, it relates to a process for coating solid forms, characterized in that it comprises the immersion of the solid forms in a film-forming composition according to the invention for the preparation of caplets.

Any technique known to a person skilled in the art, such as fluidized bed, atomization, spraying, spheronization or coating pan, can be used to carry out the film-coating of solid forms. By way of indication, it is possible to proceed as follows: the film-forming composition is used at a solids content of 10 to 30%, preferably of 15 to 20%. It is optionally precooked beforehand at 90° C. and preheated to the desired spraying temperature, generally of the order of 50-55° C. The bed of tablets is preheated to approximately 55° C. and the film-forming composition is sprayed over this bed of moving cores while maintaining a temperature of the order of 55° C.

Caplets are manufactured, for example, by the immersion of the tablets mechanically or by hand in a bath comprising the film-forming composition according to the invention.

Use may be made, for the manufacture of hard gelatin capsules, of conventional equipment, which consists in immersing metal fingers in the film-forming composition held at a constant temperature. Use may be made, for the preparation of soft capsules, of the known techniques for forming on drums or by extrusion.

Films and in particular flavor strips are manufactured, for example, by spreading the film-forming composition with a low and constant thickness over a flat or cylindrical surface, followed by drying at ambient temperature or under hot conditions. The solids content of the solution to be coated is chosen according to the drying time which it is desired to apply. By way of indication, a solids content of between 50 and 90% is generally chosen.

Films of very good quality were obtained comprising, by weight:
  10 to 15% by weight of pregelatinized and/or fluidification-treated hydroxypropylated pea starch,
  1 to 3% of glycerol.

The invention will be better understood on reading the examples which follow, which are meant to be solely illustrative and nonlimiting.

EXAMPLE 1

Film-Coating of Tablets

Various film-coating compositions with the following compositions are evaluated:

TABLE 1

| Compound | Function | Brand | Reference |
|---|---|---|---|
| Starch (cf. table 2) | Film-forming agent | Roquette | |
| Glycerol | Plasticizer | J. T. Baker | 7044 |
| Talc, very fine powder | Opacifier | Merck | Art. 8070 |
| Titanium dioxide | Opacifier | Prolabo | |
| Eurocert indigo carmine | Dye | Warner Jenkinson | 0036904 |
| Demineralized water | Vehicle | | |

The various types of starch tested:

TABLE 2

| Nature of the starch | Type |
|---|---|
| Manioc, 20% amylose | Hydroxypropylated (degree of substitution DS = 0.2) |
| Pea, 35–39% amylose | Hydroxypropylated (DS = 0.2) Acid fluidification-treated Acetylated (DS = 0.021) Hydroxypropylated (DS = 0.2) Acid fluidification-treated |
| Waxy corn, 21% amylose | Pregelatinized |
| Amylose-rich corn (70%) | Pregelatinized Hydroxypropylated |
| Mixture of waxy and amylose-rich starches, amylose content of the mixture 42% | Hydroxypropylated (DS = 0.10) amylose-rich starch and native waxy |

The tablets to be film-coated are concave tablets with a diameter of 10 mm and a mean weight of 330 mg and with a composition: 99% Pearlitol® 200SD mannitol and 1% magnesium stearate.

The following equipment is used: jacketed bowl made of stainless steel, IKA RW25W paddle mixer, UltraTurrax T25 homogenizer, peristaltic pump, coating device of fluidized air bed type, Glatt WSG 3V.

The coating solution with a solids content of 20% comprises 12.5% of starch, 1.25% of plasticizer, 6.25% of opacifier (talc and titanium dioxide), 80% of water and a negligible amount of dye.

The liquid phase is mixed and the starch is added to this mixture, subsequently heated to 90° C. The talc is added, the solution is kept stirred at 90° C. for 30 minutes and then it is cooled to the chosen spraying temperature.

For the coating of the tablets, the bed of tablets and the device are preheated to 55° C. The spraying of the film-forming solution is halted when 300 grams have actually been distributed.

The formulations are graded by comparison between the various formulations tested with +++ for the best performance and 0 for the worst performance.

The viscosities measured are Brookfield viscosities, determined for solutions with a solids content of 10% and at 25° C., by means, for example, of a Brookfield RVF 100 viscometer using the spindle of the device which gives a reading of between 20 and 80% of the scale of the dial of the device at a rotational speed of 100 revolutions per minute.

The waxy starch caused sticking very rapidly and throughout the coating, as well as the formation of agglomerates. The coating thus could not be carried out correctly, which is why no characterization of the film and of its appearance was performed.

Gelling excluded from selection the solutions based on amylose-rich starches.

The excessively high viscosity of the solution based on hydroxypropylated manioc starch also excluded it as it does not make it possible to spray correctly.

The solution based on hydroxypropylated pea starch does not retrograde, even at ambient temperature for more than 24 hours.

The combined results are taken up in the table below:

TABLE 3

| Starch | Type | Viscosity at 25° C. and 10% SC (mPa·s) | Strength of the film | Smooth appearance | Nonsticky feel | Absence of agglomerates during coating | Coating appearance |
|---|---|---|---|---|---|---|---|
| Pea starch (35/39% amylose) | Hydroxypropylated (DS = 0.2) | ++ (270) | +++ | ++ | +++ | +++ | +++ |
| | Hydroxypropylated (DS = 0.2) fluidification-treated | +++ (126) | +++ | +++ | +++ | +++ | +++ |
| | fluidification-treated Acetylated (DS = 0.021) | +++ (24) | + | +++ | +++ | ++ | + |
| Amylose-rich corn (70%) | Pregel Hydroxypropylated (DS = 0.21) | 0 (>500) | +++ | ++ | +++ | + | +++ |
| Manioc, 20% amylose | Hydroxypropylated (DS = 0.2) | 0 (>500) | – | – | – | +++ | – |
| Waxy corn, 21% amylose | Pregelatinized | (421) | nd | – | – | 0 | nd |
| Mixture of starches comprising 42% amylose | Native Amylose-rich waxy corn Hydroxypropylated (DS = 0.10) | ++ (246) | ++ | ++ | +++ | ++ | +++ |

Starches or mixtures of starches exhibiting an amylose content of between 25 and 45% and at least one stabilized starch show a marked superiority for use as film-forming agent in comparison with waxy starches or amylose-rich (more than 45%) starches. Hydroxyproylated pea starch with a degree of substitution of at most 0.2, which is optionally fluidification-treated, gives the best results. This solution could be sprayed under cold conditions over the tablets, which is particularly advantageous and gives a better appearance to the tablets than under hot conditions.

EXAMPLE 2

Preparation of Films

The following equipment is used: jacketed bowl made of stainless steel with internal circulation of oil for the heating, IKA RW25W paddle mixer, Guedu type 4.5 NO vacuum mixer, automatic film applicator.

The film-forming solutions tested have the following composition:

| Amount in grams | Formula 1 | Formula 2 |
|---|---|---|
| Pea starch, 37% amylose, hydroxypropylated (DS = 0.20), pregelatinized | 67.5 | |
| Pea starch, 37% amylose, hydroxypropylated (DS = 0.20), fluidification-treated | | 67.5 |
| Glycerol | 9.0 | |
| Mint flavoring | 7.5 | |
| Menthol | 7.5 | |
| Soybean lecithin | 0.5 | 0.75 |
| Sodium saccharinate | 2.5 | |
| Dye (1% solution) | 1.5 | |
| Water | 404 | 403.75 |

The water, the glycerol, the dye and the sodium saccharinate are mixed in the stainless steel bowl for 5 minutes. The starch is subsequently added and dispersed for 5 minutes. The mixture is heated to 70° C. and maintained at this temperature for 10 minutes, then transferred into the Guedu preheated to 40° C. and deaerated under vacuum for 5 minutes. The menthol is subsequently dissolved in the flavoring and soybean lecithin, in order to incorporate it in the Guedu, and the combined components are mixed under vacuum for 10 minutes. The composition obtained is spread according to a thickness of 0.4 mm over a Plexiglas plate using the automatic film applicator. The film obtained is dried at ambient temperature and then cut to the desired size in order to form flavor strips (sheets).

The flavor strips obtained with these two formulations exhibit a strength and a stiffness suitable for their packaging and for handling operations. Dissolution in the mouth is rapid and a high aromatic impact confers thereon a breath freshening function.

With the compositions of the prior art, such as based on native or modified amylose-rich (70%) corn starch, it is possible to obtain flavor strips exhibiting a similar texture but the high processing temperatures essential in order to prevent retrogradation of the starch and to make possible spreading of the film-forming solution result in significant evaporation of the flavoring: the flavor strips no longer have an aromatic impact and no longer have the desired "freshening" function.

With the compositions of the prior art based on starches with a high amylopectin content (waxy starches, more than 75% of amylopectin, less than 25% of amylose), the films do not exhibit the necessary cohesion: they crack on drying.

Only the film-forming compositions exhibiting an amylose content of between 25% and 45% make it possible to obtain flavor strips exhibiting the desired texture and the desired aromatic impact.

EXAMPLE 3

Film-coating of Vitamin-comprising Tablets

Various compositions in accordance with the invention are prepared for the film-coating of vitamin-comprising tablets as follows:

Composition 1

| | |
|---|---|
| Fluidification-treated hydroxypropylated pea starch: | 10.25% |
| Alginate | 0.6% |
| Lecithin | 0.38% |
| Triacetin | 0.31% |
| PEG 8000 | 0.94% |
| Lake | 1.87% |
| Titanium dioxide | 0.6% |
| Water | 85% |

Composition 2

The pea starch according to the invention was combined with a cellulose derivative so as to improve the adhesion of the composition to the tablets.

| | |
|---|---|
| Fluidification-treated hydroxypropylated pea starch: | 5.15% |
| Hydroxypropyl methylcellulose: | 5.15% |
| Alginate | 0.6% |
| Lecithin | 0.38% |
| Triacetin | 0.31% |
| PEG 8000 | 0.94% |
| Lake | 1.87% |
| Titanium dioxide | 0.6% |
| Water | 85% |

Composition 3

| | |
|---|---|
| Fluidification-treated hydroxypropylated pea starch: | 4.8% |
| Hydroxypropyl methylcellulose: | 5.25% |
| Hydroxyethyl cellulose | 1.5% |
| Titanium dioxide | 2.25% |
| Ethoxylated stearic acid | 1.2% |
| Water | 85% |

These three compositions are sprayed over vitamin C tablets. They make it possible to obtain a glossy film of excellent adhesion and make it possible to coat incised tablets with little or no filling of the logo.

What is claimed is:

1. A film-forming starchy composition for the film-coating of solid forms or for the preparation of films, wherein said composition exhibits an amylose content of between 30 and 40%, this percentage being expressed by dry weight with respect to the dry weight of starch present in said composition, and wherein said composition comprises at least one hydroxypropylated and fluidification-treated pea starch.

2. The composition as claimed in claim 1, which exhibits an amylose content of between 35 and 40%, this percentage being expressed by dry weight with respect to the dry weight of starch present in said composition.

3. The composition as claimed in claim 1 which additionally comprises a plasticizer.

4. The composition as claimed in claim 3 wherein said plasticizer is selected from the group consisting of sorbitol, glycerol, polyethylene glycol, triethyl citrate, polysorbate, carnauba wax, hydrogenated castor oil and mixtures thereof.

5. The composition as claimed in claim 1 which additionally comprises a secondary film-forming agent selected from the group consisting of cellulose derivatives, alginates, carrageenates, polyvinylpyrrolidone, poly(vinyl phthalate), dextrose, zein, pullulan, acrylic polymers, polyvinyl alcohol, gelatin, dextrins and mixtures thereof.

6. The composition as claimed in claim 1 which comprises 10 to 15% by weight of hydroxypropylated and fluidification treated pea starch and 1 to 2% by weight of plasticizer.

7. The composition as claimed in claim 1, which exhibits a viscosity of less than 500 mPa·s at 25° C. and has a solids content of 10%.

8. The composition as claimed in claim 1, which comprises at least one pharmaceutical active substance.

9. A pulverulent film-forming starchy composition for the film-coating of solid forms or for the preparation of films,
   wherein said composition exhibits an amylose content of between 30 and 40%, this percentage being expressed by dry weight with respect to the dry weight of starch present in said composition,
   wherein said composition comprises:
   from 15 to 75% by weight of hydroxypropylated and fluidification-treated pea starch, and
   from 1 to 20% by weight of a secondary film-forming agent.

10. The composition as claimed in claim 9 which additionally comprises from 1 to 20% of microcrystalline cellulose.

11. The composition as claimed in claim 9 which additionally comprises from 5 to 15% of plasticizer, by dry weight with respect to said composition.

12. The composition as claimed in claim 9, wherein the secondary film-forming agent is a cellulose derivative.

13. A process for the film-coating of solid forms, which comprises spraying a film-forming composition as claimed in claim 1 over a bed of moving cores.

14. A process for coating solid forms, which comprises immersing the solid forms in a film-forming composition as claimed in claim 1.

15. The process as claimed in claim 14, wherein said solid forms are capsules.

16. The process as claimed in claim 15, wherein the capsules are hard gelatin capsules.

17. A process for the preparation of films, which comprises spreading a film-forming composition as claimed in claim 1 over a flat or cylindrical surface, followed by drying at least at ambient temperature.

* * * * *

UNITED STATES PATENT AND TRADEMARK OFFICE
CERTIFICATE OF CORRECTION

| | | |
|---|---|---|
| PATENT NO. | : 8,652,513 B2 | |
| APPLICATION NO. | : 10/579919 | |
| DATED | : February 18, 2014 | |
| INVENTOR(S) | : Lefevre et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 684 days.

Signed and Sealed this

Twenty-ninth Day of September, 2015

Michelle K. Lee
*Director of the United States Patent and Trademark Office*